(12) United States Patent
Ahmad

(10) Patent No.: US 9,669,171 B2
(45) Date of Patent: Jun. 6, 2017

(54) PRESSURE LINE PURGING SYSTEM FOR A MECHANICAL VENTILATOR

(75) Inventor: Samir Ahmad, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1077 days.

(21) Appl. No.: 13/881,187

(22) PCT Filed: Oct. 19, 2011

(86) PCT No.: PCT/IB2011/054658
§ 371 (c)(1),
(2), (4) Date: Apr. 24, 2013

(87) PCT Pub. No.: WO2012/056373
PCT Pub. Date: May 3, 2012

(65) Prior Publication Data
US 2013/0206144 A1    Aug. 15, 2013

Related U.S. Application Data

(60) Provisional application No. 61/406,770, filed on Oct. 26, 2010.

(51) Int. Cl.
*A61M 16/20* (2006.01)
*A61M 16/00* (2006.01)
(Continued)

(52) U.S. Cl.
CPC ........ *A61M 16/0066* (2013.01); *A61M 16/00* (2013.01); *A61M 16/0051* (2013.01);
(Continued)

(58) Field of Classification Search
CPC ........ A61B 5/087; A61B 5/091; A61M 11/02; A61M 16/00; A61M 16/0051;
(Continued)

(56) References Cited

U.S. PATENT DOCUMENTS 4,527,557 A * 7/1985 DeVries ................ A61M 16/00
128/204.23
5,237,987 A * 8/1993 Anderson ............. A61M 16/00
128/204.18
(Continued)

FOREIGN PATENT DOCUMENTS

CN     101489615 A    7/2009
EP       1800707 A1   6/2007
(Continued)

*Primary Examiner* — Annette Dixon

(57) ABSTRACT

A secondary line purging system (40) having a blower (22) for pressurizing a flow of gas and a first pressure sensor (28) for measuring a first pressure of the flow of gas at or near the blower. The system also includes a secondary line (36) communicating with the blower and a subject circuit (32). The system further includes a second pressure sensor (30) for measuring a second pressure of the flow of gas within the secondary line. A valve system (42) is operable in 1) a first mode of operation to isolate the blower from the secondary line and 2) a second mode of operation to permit communication between the blower to the secondary line to purge the secondary line of obstructions with the pressurized flow of gas. A controller (16) switches operation of the valve system between the first mode of operation and the second mode of operation, based on the first pressure and the second pressure.

15 Claims, 3 Drawing Sheets

(51) Int. Cl.
*A61M 16/06* (2006.01)
*A61M 16/08* (2006.01)
*A61M 16/10* (2006.01)
*A61M 16/12* (2006.01)
*A61M 16/14* (2006.01)

(52) U.S. Cl.
CPC ........ *A61M 16/0069* (2014.02); *A61M 16/06* (2013.01); *A61M 16/0858* (2014.02); *A61M 16/0875* (2013.01); *A61M 16/104* (2013.01); *A61M 16/12* (2013.01); *A61M 16/14* (2013.01); *A61M 16/20* (2013.01); *A61M 16/202* (2014.02); *A61M 16/204* (2014.02); *A61M 2016/0021* (2013.01); *A61M 2016/0027* (2013.01); *A61M 2205/3331* (2013.01); *A61M 2205/502* (2013.01); *A61M 2205/52* (2013.01)

(58) Field of Classification Search
CPC .......... A61M 16/0066; A61M 16/0069; A61M 16/10; A61M 16/12; A61M 16/125; A61M 16/16; A61M 16/20; A61M 16/202; A61M 16/204; A61M 16/205; A61M 16/206; A61M 2016/0021; A61M 2016/0039; A61M 2016/0042; A61M 2205/15; A61M 2205/16; A61M 2205/42; A61M 2205/505; A61M 2205/7518; A61M 2205/8206
USPC ............ 128/200.11, 204.18, 204.21, 204.23, 128/204.25, 205.24, 205.25, 207.29; 600/532, 538
See application file for complete search history.

(56) References Cited

U.S. PATENT DOCUMENTS

| | | | |
|---|---|---|---|
| 6,152,135 | A | 11/2000 | DeVries |
| 6,203,502 | B1 | 3/2001 | Hilgendorf |
| 6,450,164 | B1 | 9/2002 | Banner |
| 6,546,930 | B1* | 4/2003 | Emerson ........... A61M 16/0051 128/204.18 |
| 6,644,310 | B1* | 11/2003 | Delache ................ A61M 16/00 128/204.18 |
| 6,945,248 | B2* | 9/2005 | Berthon-Jones ...... A61M 16/00 128/200.24 |
| 2004/0003814 | A1 | 1/2004 | Banner |
| 2006/0144396 | A1 | 7/2006 | DeVries et al. |
| 2006/0249153 | A1 | 11/2006 | DeVries |
| 2007/0113847 | A1 | 5/2007 | Acker |
| 2008/0011300 | A1* | 1/2008 | Andreiux .............. A61M 16/10 128/204.21 |
| 2009/0260631 | A1* | 10/2009 | Aubonnet ................ A62B 7/14 128/205.25 |
| 2010/0051026 | A1 | 3/2010 | Graboi |
| 2010/0252048 | A1 | 10/2010 | Young |

FOREIGN PATENT DOCUMENTS

| | | |
|---|---|---|
| WO | 0032261 A1 | 6/2000 |
| WO | 0195972 A2 | 12/2001 |
| WO | 2008008163 A2 | 1/2008 |

* cited by examiner

PRESSURE LINE PURGING SYSTEM FOR A MECHANICAL VENTILATOR

BACKGROUND OF THE INVENTION

1. Field of the Invention

The invention relates to a pressure or secondary line purging system and method for a mechanical ventilator.

2. Description of the Related Art

Ventilators are commonly used to ventilate a subject's lungs with respiratory gas to assist the subject in breathing. The ventilator may be operatively connected to a subject circuit that is adapted to communicate the flow of gas to an airway of the subject at a subject interface. A pressure line may be operatively connected to the ventilator and may be in fluid communication with the subject circuit at or near the subject interface. A sensor is typically provided that senses the pressure of the flow of gas within the pressure line. The pressure measurements are used to control pressure at the patient, triggering of breaths, and in calculations of parameters in lung mechanics, such as the calculation of work of breathing and lung compliance. The pressure measurements may also be used to assist in controlling the support supplied by a ventilator so as to assist the subject in breathing.

However, during use, the pressure lines may become obstructed with fluid (e.g., water and/or mucous) from the subject. The obstruction may result in erroneous airway pressure readings. Accordingly, there may be insufficient ventilation of the patient. Furthermore, water and/or mucous from the subject may also flow through the pressure line and into the ventilator, which may interfere with the operation of the ventilator.

Conventional purging systems for purging the pressure line of obstruction are known. Conventional purging systems typically include a separate compressor or a secondary source of pressurized gas to purge the pressure lines. Thus, these conventional purging systems may often be bulky, complicated, and expensive to manufacture.

SUMMARY OF THE INVENTION

One aspect of the invention relates to a secondary line purging system having a blower configured to pressurize a flow of gas for delivery to a subject. The blower includes a variable speed motor connected to a fan having an outlet. The secondary line purging system also includes a first pressure sensor configured to measure a first pressure of the flow of gas at or near the blower and a subject circuit operatively connected to the outlet. The subject circuit is adapted to communicate the flow of gas to an airway of the subject at a subject interface. The system also includes a secondary line in fluid communication with the blower and the subject circuit at or near the subject interface. The system further includes a second pressure sensor configured to measure a second pressure of the flow of gas within the secondary line. A valve system is configured to be operable in 1) a first mode of operation to isolate the blower from the secondary line and 2) a second mode of operation to permit fluid communication between the blower to the secondary line so as to purge the secondary line of obstructions with the pressurized flow of gas. A controller is configured to switch operation of the valve system between the first mode of operation and the second mode of operation, based on the first pressure and the second pressure, such that the valve system is placed in the second mode of operation responsive to a difference between the first pressure and the second pressure breaching a threshold.

Another aspect of the invention relates to a method for purging a secondary line, the method includes the step of pressurizing a flow of gas for delivery to a subject. The pressurized flow of gas is provided by a blower comprising a variable speed motor connected to a fan having an outlet. The method also includes the steps of communicating the flow of gas to an airway of the subject at a subject interface. The communication is provided by a subject circuit operatively connected to the outlet. The method further includes the steps of sensing a first pressure of the flow of gas at or near the blower and sensing a second pressure of the flow of gas within a secondary line that is in fluid communication with the blower and the subject circuit at or near the subject interface. The method also includes controlling the operation of a valve system between 1) a first mode of operation to isolate the blower from the secondary line and 2) a second mode of operation to permit fluid communication between the blower to the secondary line so as to purge the secondary line of obstructions with the pressurized flow of gas, based on the first pressure and the second pressure, such that the valve system is placed in the second mode of operation responsive to a difference between the first pressure and the second pressure breaching a threshold.

Yet another aspect of the invention relates to a secondary line purging system having means for pressurizing a flow of gas for delivery to a subject. The pressurized flow of gas is provided by a blower comprising a variable speed motor connected to a fan having an outlet. The system also includes means for communicating the flow of gas to an airway of the subject at a subject interface. The means for communication is provided by a subject circuit operatively connected to the outlet. The system also includes means for sensing a first pressure of the flow of gas at or near the blower and means for sensing a second pressure of the flow of gas within a secondary line that is in fluid communication with the blower and the subject circuit at or near the subject interface. The system further includes means for controlling the operation of a valve system between 1) a first mode of operation to isolate the blower from the secondary line and 2) a second mode of operation to permit fluid communication between the blower to the secondary line so as to purge the secondary line of obstructions with the pressurized flow of gas, based on the first pressure and the second pressure, such that the valve system is placed in the second mode of operation responsive to a difference between the first pressure and the second pressure breaching a threshold.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein can be considered drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENT

Figure 1:
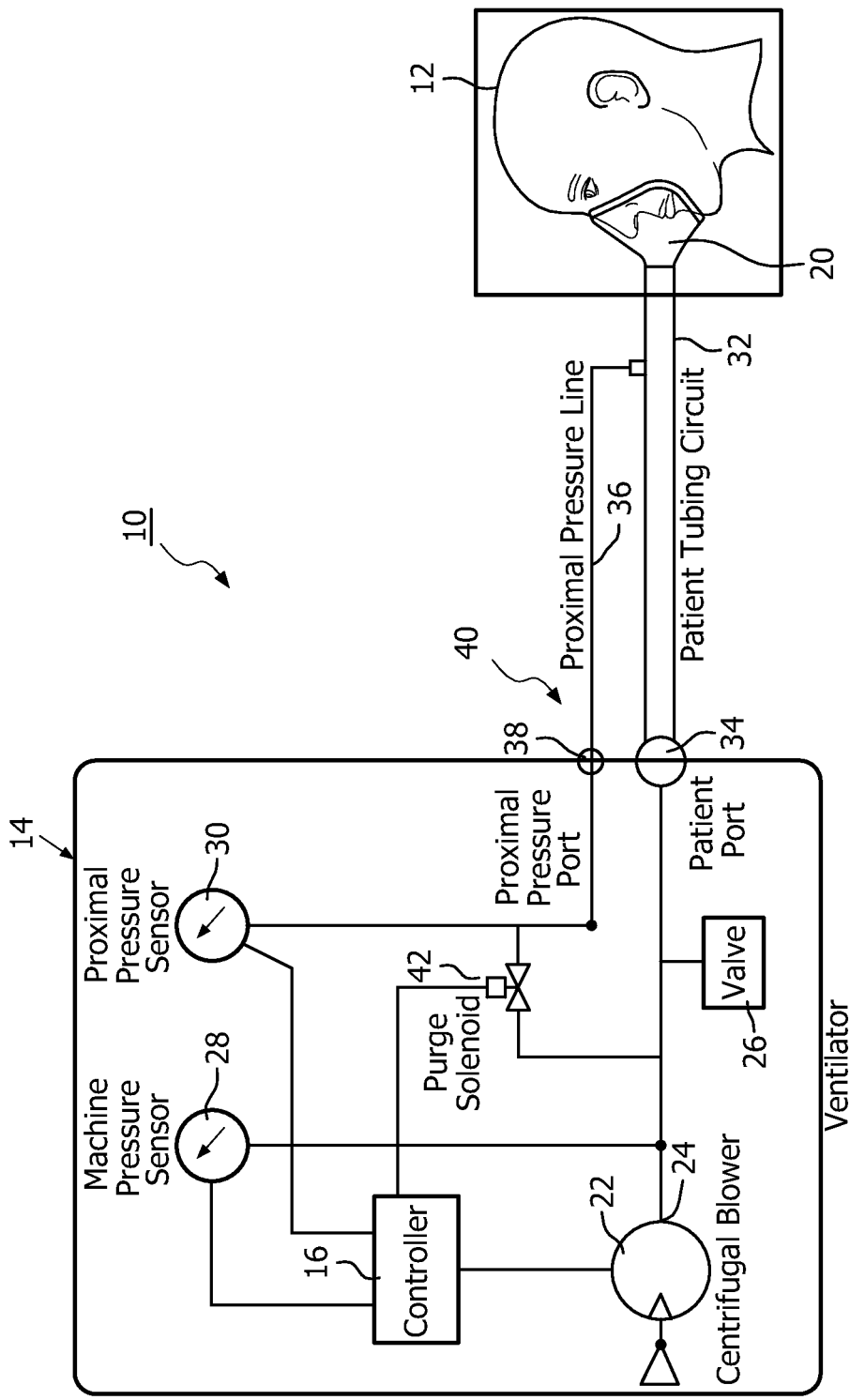
FIG. 1 illustrates a gas delivery system having a secondary line purging system in accordance with an embodiment.

FIG. 1 illustrates a system 10 configured to deliver a pressurized flow of breathable gas to the airway of a subject 12. The gas delivery system 10 includes a ventilator 14 that provides pressurized flow of breathable gas to the airway of subject 12 such that one or more gas parameters of the pressurized flow of breathable gas provide therapeutic benefit to the subject 12. In one embodiment, the system 10 is configured such that the pressurized flow of breathable gas supports the airway of subject 12 to permit subject 12 to breathe. In one embodiment, the system 10 is configured such that the respiration of subject 12 is mechanically assisted by the pressurized flow of breathable gas. To enhance the effectiveness in facilitating respiration by the subject 12, the subject's breathing parameters and/or other parameters are detected and implemented in controlling the support supplied by the ventilator 14. The ventilator 14 includes one or more of a blower 22, a control valve 26, a patient port 34, a proximal pressure port 38, a first pressure sensor 28, a second pressure sensor 30, a valve system 42, a controller 16, and/or other components.

The gas delivery system 10 includes a pressure generator including blower 22 that receives a supply of breathing from a breathing gas source (not shown) and elevates the pressure of that gas for delivery to the airway of the subject 12. The gas source can be provided in the same housing as the ventilator 14, or may be separate and connected thereto. According to some embodiments, the respiratory gas from the gas source is delivered with supplemental oxygen from an oxygen source to elevate the level of oxygen concentration in the gas delivered to the subject 12. This may include mixing the breathable gas from gas source with the supplemental oxygen at the ventilator 14, or downstream from the ventilator 14. The breathing gas for delivery to the patient can be any respiratory gas, such as air, oxygen, or an oxygen mixture (e.g., heliox). The breathing gas may also include a mixture of a breathable gas and a medication, which can be in gaseous form (e.g., nitric oxide) or nebulized.

The blower 22 includes a constant or variable speed motor (not shown) connected to a fan (not shown) having an outlet 24. In one embodiment, the speed of the blower 22 may be rapidly increased or decreased depending on a desired rate of flow. This enables each inspiration and exhalation to be controlled with greater flexibility. For example, the blower 22 enables the gas flow to change rapidly to allow the ventilator to vary the rate of flow multiple times or continuously within the time span of a single breath. Accordingly, the ventilator 14 can make rapid and repeated adjustments to respond accordingly to the patient's breathing parameters or other parameters.

The elevated pressure flow of breathing gas from the blower 22 is delivered to the control valve 26 downstream of the blower 22. The control valve 26, either alone or in combination with blower 22, controls the final pressure or flow of gas exiting the ventilator 14. Examples of a suitable pressure/flow controller include at least one valve, such as sleeve or poppet valve, that exhausts gas from the patient circuit as a method of controlling the pressure in the patient circuit. Other suitable pressure/flow controllers are believed to be well known to those skilled in the art. Some embodiments (not depicted) may not include the control valve 26. In such embodiments, the final pressure exiting the pressure/flow generating system is controlled by the blower 22.

In embodiments in which the blower 22 is a blower that operates at all times at only one speed, the control valve 26 alone can be used to control the final pressure and flow rate for the breathing gas delivered to the patient. In some embodiments, however, the operating speed of the blower 22 is controlled in combination with control valve 26 to control the final pressure and flow rate for the breathing gas delivered to the patient. For example, a pressure or flow rate close to the desired pressure or flow rate can be set by establishing an appropriate operating speed for the blower 22 along with the control valve 26 so that the two, operating together, determine the final pressure for the breathing gas delivered to the patient.

The flow of breathing gas is carried from the ventilator 14 to the subject 12 via a subject circuit 32, which is typically a single flexible tube or conduit that carries the flow of breathing gas to a patient interface assembly 20. The subject circuit 32 may be connected to the outlet 24 of the blower 22. Accordingly, the gas from the blower 22 may be communicated to the subject circuit 32 via a patient port 34 provided in the ventilator 14. The patient interface assembly 20 may include a patient interface appliance—either invasive or non-invasive—such as a nasal mask, nasal/oral mask, total face mask, nasal cannula, endotracheal tube, or tracheal tube, suitable for communicating a supply of breathing gas to the airway of a patient. The patient interface assembly 20 may also include a headgear assembly, such as mounting straps or a harness. The patient interface assembly 20 may also include controls thereon, and other attributes. In some embodiments, the patient interface assembly 20 and/or patient circuit 32 may optionally include a suitable exhaust port (not shown) for exhausting gas from these components to ambient atmosphere. The exhaust port may be a passive exhaust port in the form of a continuously open port that imposes a flow restriction on the exhaust gas to permit control of the pressure of gas within patient interface assembly 20. It is to be understood, however, that exhaust port can be an active exhaust port that assumes different configurations to control the exhaust rate.

The system 10 also includes a pressure line 36 that is in fluid communication with the ventilator 14 and the subject circuit 32 at or near the subject interface assembly 20. The pressure line may be formed from a tubular conduit. In one embodiment, the pressure line 36 delivers a flow of gas to the ventilator 14 through a proximal pressure port 38 in the ventilator to permit the pressure at or near patient interface assembly 20 to be determined.

The sensors 28 and 30 are configured to determine one or more parameters associated with the breathing gas output. The first pressure sensor 28 is configured to measure a first pressure of the flow of gas near or at the blower 22. The proximal pressure sensor 30 in the ventilator 14 is configured to measure the pressure of the flow of gas within the pressure line 36. Since the pressure line 36 communicates with the subject circuit 32 at or near the airway of subject 12, the pressure measured by proximal pressure sensor 30 (e.g., a second pressure) is the pressure of the flow of gas within the subject circuit 32 at a proximal location to the subject's airway. The proximal pressure sensor 30 in the ventilator 14 is configured to measure the pressure of the flow of gas within the pressure line 36.

Other sensors may optionally be provided, such as sensors configured to determine one or more of the instantaneous volume of gas delivered to the patient, the instantaneous flow rate of gas delivered to the patient, the pressure of gas delivered to the patient, the temperature of gas delivered to the patient, the humidity of gas delivered to the patient, or any other parameter associated with gas delivered to the patient. The pressures sensed by the sensors 28, 30 may be communicated to the controller 16. In some embodiments, the pressure sensors 28, 30 may generate pressure signals representative of the sensed first and second pressures, and the pressure signals may be transmitted through an A/D converter (not shown) to the controller 16. The pressure sensors 28, 30 may be any known pressure sensor, for example, a pressure transducer, a piezoresistive pressure sensor, a solid state pressure sensor, or any other type of sensors capable of measuring pressure and generating signals representative of the measured pressure.

The electronic controller 16 controls the various operating aspects of the ventilator 14. For example, the outputs of the sensors 28, 30 are provided to the controller 16 for processing, if needed, to determine one or more parameters associated with the breathing gas output. It should be appreciated that the controller 16 may refer to a single controller or more than one controller. A control interface (not shown) may be used to provide data and commands to the controller 16 of the ventilator 14. The control interface may include any device suitable to provide information and/or commands to the controller 16 via a hardwire or wireless connection. Typical examples of the control interface may include a keypad, keyboard, touch pad, mouse, microphone, switches, button, dials, or any other devices that allow a user to input information to the delivery system 10. In one embodiment, the controller 16 comprises a processor that is suitably programmed with the necessary algorithm or algorithms for calculating gas parameters (e.g., pressure, temperature, humidity, flow, etc.) to be applied to gas delivered to the patient according to various modes of ventilation.

In one embodiment, the ventilator 14 optionally includes electronic storage (not shown) associated with the controller 16 for storing the programming necessary to perform any of a plurality of modes of ventilation, depending on which mode of ventilation is selected by the caregiver or patient using the control interface. The electronic storage may also be capable of storing data regarding the operation of the gas delivery system 10, input commands, alarm thresholds, as well as any other information pertinent to the operation of the gas delivery system 10, such as measured values of gas flow, volume, pressure, device usage, operating temperatures, and motor speed. In some embodiments, the parameters and data obtained during operation of the gas delivery system 10 may be stored in the electronic storage to provide a permanent log of parameters and data that relate to the subject's course on the ventilator 14, and allow for analysis of the operation of the gas delivery system 10. The electronic storage may include storage that is provided integrally (i.e., substantially non-removable) and/or removable storage that is removably connectable to the system 10 via, for example, a port (e.g., a USB port, a firewire port, etc.) or a drive (e.g., a disk drive, etc.). Electronic storage may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage may store software algorithms, information determined by the controller 16, information received via user interface, and/or other information that enables system 10 to function properly. Electronic storage may be (in whole or in part) a separate component within system 10, or electronic storage may be provided (in whole or in part) integrally with one or more other components of system 10.

A purging system 40 is provided in the gas delivery system 10 to purge the pressure line 36 of obstruction (e.g., water and/or mucous). In one embodiment, the purging system 40 includes one or more of the blower 22, the first pressure sensor 28, the proximal pressure sensor 30, the subject circuit 32, the pressure line 36, a valve system 42 provided between the pressure line 36 and the blower 22, the controller 16, and/or other components. It should be appreciated that although the purging system 40 is described herein with respect to a pressure line, this is not intended to be limiting. The scope of this disclosure includes any secondary line that communicates the subject circuit 32 at or near the airway of the subject 12 with the ventilator 14.

In one embodiment, the valve system 42 is disposed between the pressure line 36 and the blower 22 such that the flow of gas is communicated from the blower 22 to the pressure line 36 through the valve system 42. The valve system 42 is configured to be operable in 1) a first mode of operation to isolate the blower 22 from the pressure line 36 and 2) a second mode of operation to permit fluid communication between the blower 22 to the pressure line 36 so as to purge the pressure line 36 of obstructions with the pressurized flow of gas. The pressurized flow of gas through from the blower 22 through the pressure line 36 may remove obstructions within the pressure line 36. That is, the blower 22 enables an "opposite" flow of pressurized gas through the pressure line 36 to dislodge and remove any obstructions that may be interfering with, blocking, or obstructing the normal flow of fluid through the pressure line 36. Accordingly, this configuration enables the purging of the pressure line 36 without the use of a secondary compressor or other secondary sources of pressurized gas. However, it is contemplated that in some embodiments, a secondary source of pressurized gas may also be provided to facilitate operations of the purging system 40.

In some embodiments, the controller 16 is configured to switch operation of the valve system between the first mode of operation and the second mode of operation, based on the first pressure (i.e., the pressure at the ventilator 14) sensed by the first pressure sensor 28 and the second pressure (i.e., the proximal pressure) sensed by the proximal pressure sensor 30, such that the valve system 42 is placed in the second mode of operation responsive to a difference between the first pressure and the second pressure breaching a threshold. The valve system 42 may be placed in the second mode of operation responsive to the second pressure exceeding the first pressure by the threshold. In some embodiments, the threshold value may be about 2, 3, 4, 5, or 6 cm $H_2O$, although other values are contemplated. In some embodiments, the threshold value may be set by the user via the control interface. Alternatively or additionally, the threshold value may be preprogrammed into the controller 16.

In one embodiment, the valve system 42 may include a solenoid. In such an embodiment, the solenoid valve may be controlled by electric current applied thereto by the controller 16. In some embodiments, the controller 16 may provide a pulse width modulated (PWM) signal to the solenoid. The solenoid may include two ports such that in the first mode of operation, the valve is switched to a closed configuration wherein the flow of gas through the valve system 42 is prevented and in the second mode of operation (which may also be referred to as a purging operation), the valve system 42 is switched to an open configuration wherein the flow of gas through the valve system 42 is permitted. It should be appreciated, however, that this example is not intended to be limiting and that other electromechanical valves or other types of valves may be used.

Figure 2:
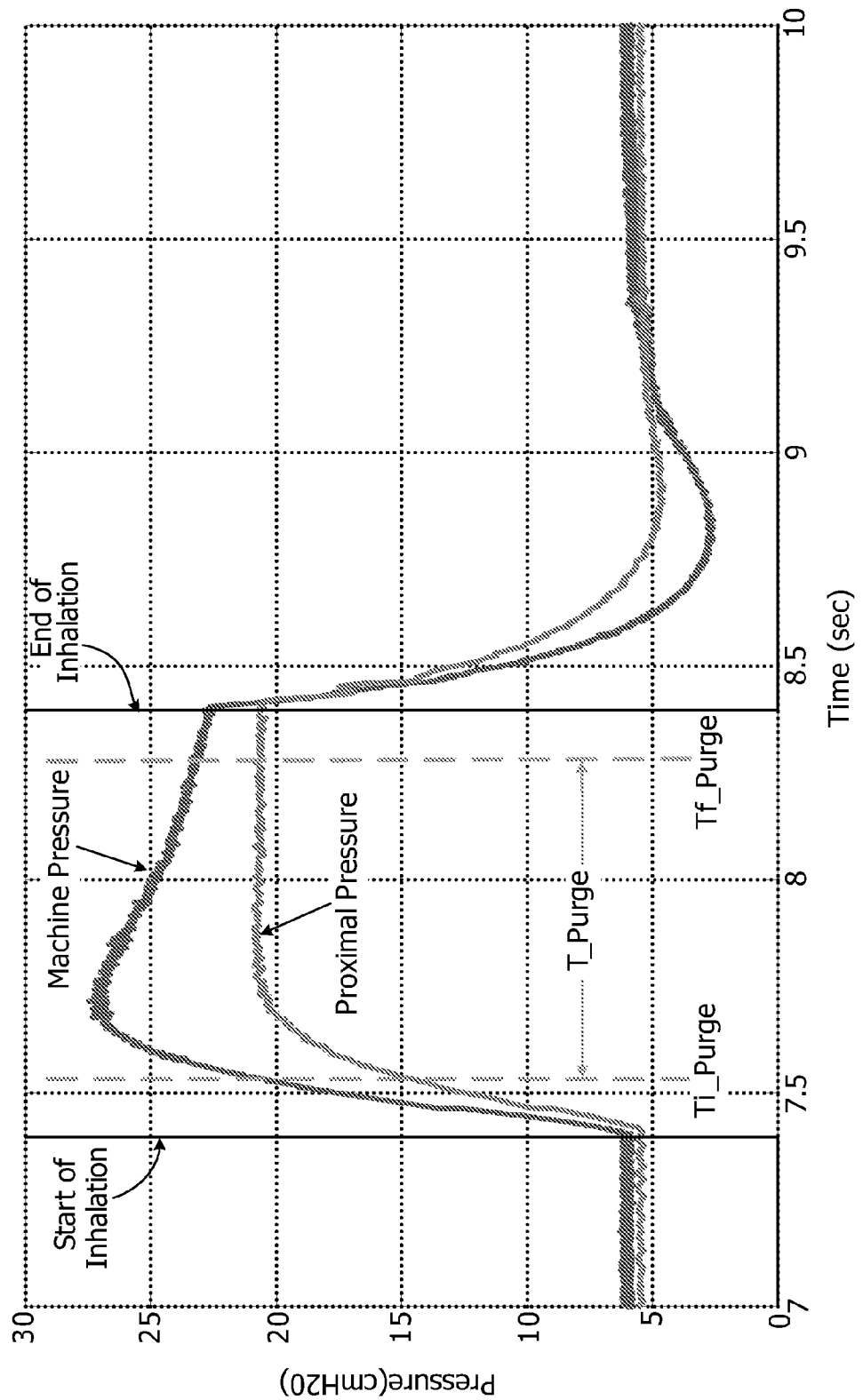
FIG. 2 illustrates a plot of a first pressure sensed by a first pressure sensor and a second pressure sensed by second pressure sensor in accordance with an embodiment.

As shown in FIG. 2, the first pressure at the ventilator 14 is typically less than or equal to the pressure in the pressure line 36 during exhalation. However, during inhalation, the first pressure at the ventilator 14 may exceed the pressure in the pressure line 36 by at least the threshold, thus placing the valve system 42 in the second mode of operation wherein gas is permitted to flow from the blower 22 to the proximal pressure line 36. However, this example is not intended to be limiting, and it is contemplated that the second mode of operation (i.e., the purging operation) may occur any time during exhalation or inhalation in other embodiments.

Figure 3:
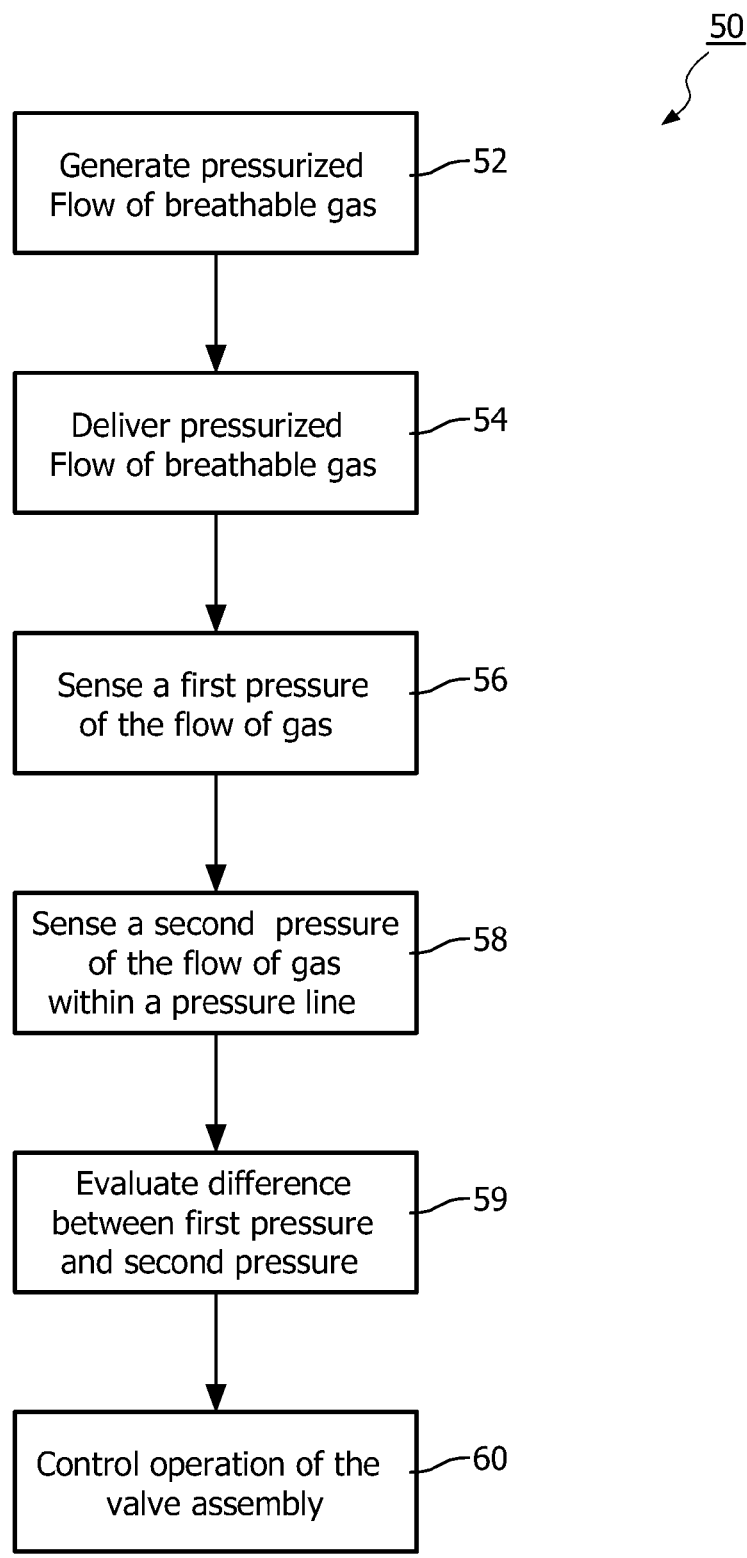
FIG. 3 illustrates an operation of the purging system in accordance with an embodiment.

FIG. 3 illustrates a method 50 of purging the pressure line 36 in accordance with an embodiment. The operations of method 50 presented below are intended to be illustrative. In some embodiments, the method 50 may be accomplished with one or more additional operations not described, and/or without one or more of the operations discussed. Additionally the order in which the operations of method 50 as illustrated in FIG. 3 and described below is not intended to be limiting.

At operation 52, a pressurized flow of breathable gas is generated. One or more gas parameters of the pressurized flow of breathable gas are controlled to provide a therapeutic benefit to the subject. In one embodiment, operation 52 is performed by a blower similar to or the same as the blower 22 (shown in FIG. 1 and described above).

At operation 54, the pressurized flow of breathable gas is delivered to the airway of the subject 12. In one embodiment, the operation 54 is performed by the subject circuit 32 shown in FIG. 1 and described above.

At operation 56, the first pressure sensor 28 senses the first pressure of the flow of gas at or near the blower 22. The first pressure sensor 28 generates signals of this pressure reading and transmits the signals to the controller 16.

At operation 58, the second pressure sensor 30 senses the second pressure of the flow of gas within the pressure line 36. As mentioned above, the pressure line 36 is connected to the subject circuit 32 at or near the subject interface assembly 20, and thus the pressure sensed by the second pressure sensor 30 is the pressure of the flow of gas at or near the subject interface assembly 20. The second pressure sensor 30 generates signals of this pressure reading and transmits the signals to the controller 16.

At operation 59, the controller 16 evaluates the difference between the first pressure sensed by the first pressure sensor 28 and the second pressure sensed by the second pressure sensor 30. For example, the controller 16 determines whether the difference between the first pressure and the second pressure breaches a predetermined threshold value, as mentioned above. In one embodiment, the controller 16 determines whether the second pressure exceeds the first pressure by the predetermined threshold value.

At operation 60, the controller 16 controls the valve assembly 42 based on the evaluation of the difference between the first pressure sensed by the first pressure sensor 28 and the second pressure sensed by the proximal pressure sensor 30. As mentioned above, the valve system 42 is configured to be operable in 1) a first mode of operation to isolate the blower 22 from the pressure line 36 and 2) a second mode of operation to permit fluid communication between the blower 22 to the pressure line 36 so as to purge the pressure line 36 of obstructions with the pressurized flow of gas. If the controller 16 determines that the difference between the first pressure (i.e., the pressure at the ventilator 14) exceeds the second pressure (i.e., the proximal pressure) by the threshold value, the controller 16 switches operation of the valve system 42 to the second mode of operation (i.e., the purging operation). Alternatively, if the controller 16 determines that the difference between the first pressure (i.e., the pressure at the ventilator 14) and the second pressure (i.e., the proximal pressure) is less than the threshold value, the controller 16 places the valve system 42 in the first mode of operation. Accordingly, when the valve system 42 is in the first mode of operation, mucous and/or water from the subject is prevented from being communicated to the blower 22 through the pressure line 36.

Alternatively or additionally, in some embodiments, the purging system 40 may also purge the pressure line 36 using other methods. For example, in some embodiments, the purging system 40 may switch the mode of the valve system between the first mode of operation and the second mode of operation based on predetermined time periods. In such embodiments, the purging system 40 may include a timer. In such embodiments, a signal may be generated by the controller 16 to the valve system 42 to switch operation between the first mode of operation to the second mode of operation (i.e., the purging operation). The valve system 42 may operate in the second mode of operation for a predetermined period of time, which may be selected by the user or determined by the controller 16. In some embodiments, the time period for the purging operation may occur during at least a portion of patient inhalation. Thus, in embodiments where the valve system 42 include a solenoid valve, the solenoid valve may be opened during inhalation for a predetermined amount of time and then may be closed before inhalation ends and exhalation occurs.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A secondary line purging system comprising:
   a blower configured to pressurize a flow of gas for delivery to a subject, the blower comprising a motor connected to a fan having an outlet;
   a first pressure sensor configured to measure a first pressure of the flow of gas at or near the blower;
   a subject circuit operatively connected to the outlet, the subject circuit adapted to communicate the flow of gas to an airway of the subject at a subject interface;
   a secondary line in fluid communication with the blower and the subject circuit at or near the subject interface;
   a second pressure sensor configured to measure a second pressure of the flow of gas within the secondary line;

a valve system configured to be operable in 1) a first mode of operation to isolate the blower from the secondary line and 2) a second mode of operation to permit fluid communication between the blower to the secondary line so as to purge the secondary line of obstructions with the pressurized flow of gas; and a controller configured to switch operation of the valve system between the first mode of operation and the second mode of operation, based on the first pressure and the second pressure, such that the valve system is placed in the second mode of operation responsive to a difference between the first pressure and the second pressure breaching a threshold, wherein the valve system is in the second mode of operation during patient inhalation such that obstructions in the secondary line are purged from the secondary line toward the subject circuit.

2. The system of claim 1, wherein the valve system is placed in the second mode of operation responsive to the second pressure exceeding the first pressure by the threshold.

3. The system of claim 1, wherein the threshold is 5 cm H2O.

4. The system of claim 1, wherein the valve system comprises a solenoid.

5. The system of claim 1, wherein the obstructions comprise one or both of water and mucous.

6. A method for purging a secondary line, the method comprising:

pressurizing a flow of gas for delivery to a subject, the pressurized flow of gas being provided by a blower comprising a motor connected to a fan having an outlet;

communicating the flow of gas to an airway of the subject at a subject interface, the communication provided by a subject circuit operatively connected to the outlet;

sensing a first pressure of the flow of gas at or near the blower; sensing a second pressure of the flow of gas within a secondary line that is in fluid communication with the blower and the subject circuit at or near the subject interface; and controlling the operation of a valve system between 1) a first mode of operation to isolate the blower from the secondary line and 2) a second mode of operation to permit fluid communication between the blower to the secondary line so as to purge the secondary line of obstructions with the pressurized flow of gas, based on the first pressure and the second pressure, such that the valve system is placed in the second mode of operation responsive to a difference between the first pressure and the second pressure breaching a threshold, wherein the valve system is in the second mode of operation during patient inhalation such that obstructions in the secondary line are purged from the secondary line toward the subject circuit.

7. The method of claim 6, wherein the valve system is placed in the second mode of operation responsive to the second pressure exceeding the first pressure by the threshold.

8. The method of claim 6, wherein the threshold is 5 cm H2O.

9. The method of claim 6, wherein the valve system comprises a solenoid.

10. The method of claim 6, wherein the obstructions comprise one or both of water and mucous.

11. A secondary line purging system comprising:

means for pressurizing a flow of gas for delivery to a subject, the pressurized flow of gas being provided by a blower comprising a motor connected to a fan having an outlet;

means for communicating the flow of gas to an airway of the subject at a subject interface, the communication provided by a subject circuit operatively connected to the outlet;

means for sensing a first pressure of the flow of gas at or near the blower;

means for sensing a second pressure of the flow of gas within a secondary line that is in fluid communication with the blower and the subject circuit at or near the subject interface; and means for controlling the operation of a valve system between 1) a first mode of operation to isolate the blower from the secondary line and 2) a second mode of operation to permit fluid communication between the blower to the secondary line so as to purge the secondary line of obstructions with the pressurized flow of gas, based on the first pressure and the second pressure, such that the valve system is placed in the second mode of operation responsive to a difference between the first pressure and the second pressure breaching a threshold, wherein the valve system is in the second mode of operation during patient inhalation such that obstructions in the secondary line are purged from the secondary line toward the subject circuit.

12. The system of claim 11, wherein the valve system is placed in the second mode of operation responsive to the second pressure exceeding the first pressure by the threshold.

13. The system of claim 11, wherein the threshold is 5 cm H2O.

14. The system of claim 11, wherein the valve system comprises a solenoid.

15. The system of claim 11, wherein the obstructions comprise one or both of water and mucous.

* * * * *